United States Patent [19] [11] 4,282,217
Baglioni et al. [45] Aug. 4, 1981

[54] PHARMACEUTICAL COMPOSITIONS CONTAINING A CORTICOSTEROID SUBSTANCE

[75] Inventors: Alessandro Baglioni, Monza; Giancarlo Sportoletti, Milan, both of Italy

[73] Assignee: Italfarmaco S.p.A., Milan, Italy

[21] Appl. No.: 162,686

[22] Filed: Jun. 25, 1980

[30] Foreign Application Priority Data

Dec. 28, 1979 [IT] Italy ............................. 28417 A/79

[51] Int. Cl.$^3$ ............................................. A61K 31/56
[52] U.S. Cl. ................................................... 424/240
[58] Field of Search ......................................... 424/240

[56] References Cited

U.S. PATENT DOCUMENTS 3,320,125  5/1967  Grim ..................................... 424/240

OTHER PUBLICATIONS

Chem. Abstracts, vol. 75, (1971), Par. 133,006(b).

Primary Examiner—Elbert L. Roberts
Attorney, Agent, or Firm—Bucknam and Archer

[57] ABSTRACT

Pharmaceutical compositions containing a corticosteroid and an ester of L-arginine with an aliphatic alcohol exhibit a synergistic effect in the protection against shock. The corticosteroid may be 6-α-methylprednisolone-21-hemisuccinate sodium salt and the L-arginine ester may be the methyl ester in the form of the hydrochloride salt.

4 Claims, No Drawings

PHARMACEUTICAL COMPOSITIONS CONTAINING A CORTICOSTEROID SUBSTANCE

The present invention relates to natural corticosuprarenal hormones and their synthetic derivatives. It is well known that these hormones exhibit a very high therapeutic activity, but the bioloigical activity of these compounds unfortunately lack in specificity and this lack in specificity of activity is probably responsible for several side effects which are observed during treatment with cortisone and cortisone type compounds. Obviously, it has been desirable to fine compositions which include cortisone and cortisone-type compounds and derivatives of cortison-type compounds and which are more specific in therapeutic activity, so that the treatment may be effective even at a lower dosage. Clearly, if the object of improving the specificity of cortisone and cortisone-type compounds is achieved, it will be possible to decrease the side effects and to achieve effective treatment at a lower dosage.

The crux of the present invention resides in the finding that the therapeutic activity of 6-α-methyl-prednisolone-21-hemisuccinate, which is considered as a typical case of corticosteroid substances, is substantially increased in a pharmaceutical preparation which contains, in addition to the corticosteroid, also an ester of L-arginine with an aliphatic alcohol. The amount of the L-arginine ester which is necessary to cause the synergistic effect may vary over a wide range, but molar ratio of the two substances of 1:1 may be used.

In patent application filled in Italy, Patent Application No. 28416 A/79, filed on Dec. 28, 1979, the therapeutic activity of arginine esters with aliphatic alcohols has been described, the arginine ester having the general formula:

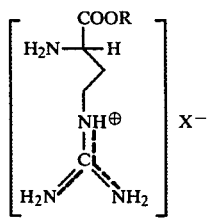

in which X⁻ is an organic or inorganic pharmaceutically acceptable anion and R is an alkyl group. In the same Italian Patent Application mentioned hereinabove, it has been stated that the pharmaceutical compositions are obtained by dissolving the individual compounds in water at a pH preferably between 5.5 and 8.5, or by using a corresponding salt formed from an organic or inorganic acid.

It has now been found that pharmaceutical preparations which contain, for instance 6-α-methyl-prednisolone-21-hemisuccinate in the form of its sodium salt or an equivalent salt together with an ester of L-arginine with an aliphatic alcohol, in the form of a salt, for instance the hydrochloride salt, exhibit an activity substantially greater in the protection from shock caused by endotoxins and anaphylactic shock, which activity is substantially greater than the activity resulting from some of the individual components, used separately. More specifically, with an equal dose, the effect of protection achieved in accordance with the present invention is substantially greater than what may be foreseen on the basis of the activity of the compounds used separately. It is, therefore, obvious that the combination of the corticosteroid and the arginine ester results in a synergism of the therapeutical effects.

The tests reported hereinbelow domenstrate the therapeutic activity of the pharmaceutical composition in accordance with the present invention.

Increase of the protective effect of 6-α-methyl-prednisolone-21-hemisuccinate sodium salt with respect to shock caused by endotoxins The endotoxin shock has been induced in accordance with the method reported by A. Bertelli and L. Donati "The Influence of Some Enzymes and Enzymes Inhibitors in Shock", "SHOCK Biochemical, Pharmaceutical and Clinical Aspects", A. Bertelli and N. Back Editors, *Advances in Experimental Medicine and Biology,* Volume 9—Plenum Press, New York—London (1970) page 215.

There are used for the test male Wistar rats of 120±10 grams by weight, previously stabilized for a period of ten days at a temperature of 21°±1° C. under conditions of controlled diet and water "ad libitum". Twenty-four hours prior to the test, the animals are divided into groups of ten, for the purpose of achieving randomization. Each dose has been tested on six groups of animals.

Lipopolysaccharide B from S. Enteritidis (Difco Labs.) has been used as the endotoxin which has been administered to the animals by the endoperitoneal route in a dose of 10 mg/kg. The administration has been carried out one hour after the administration by the parenteral route of the substance being tested or one hour after the administration of physiological saline solution in equal volume per kilogram of body weight of the animal, in the animals being used as control.

The percentage of mortality has been determined in the animals being treated with reference to the animals being used as control after twenty-four hours. The results are reported hereinbelow in Table No. 1.

TABLE 1

| COMPOUND | DOSE, mg/kg | % MORTALITY |
|---|---|---|
| 6-α-M-P* | 2.5 | 43.3 |
| 6-α-M-P | 5 | 20.0 |
| 6-α-M-P | 15 | 0.0 |
| 6-α-M-P + L-A.M.** | 2.5 + 1.3 | 21.0 |
| 6-α-M-P + L-A.M.** | 5 + 2.6 | 13.3 |
| 6-α-M-P + L-A.M.** | 2.5 + 6.3 | 0.0 |

*6-α-M-P = 6-α-methylprednisolone-21-hemisuccinate, sodium salt
**L-A.M. = L-arginine methylester hydrochloride
Amoumt of Administration: 0.12 ml/rat Increase of the effect of 6-α-methyl-prednisolone-21-hemisuccinate sodium salt against anaphylactic shock The anaphylactic shock has been caused according to the method of S. M. Feimberg, J. Pharmacol. Exp. Therap., 99, 195 (1950). There are used for the test male albino guinea pigs of average weight 350±20 grams, previously stabilized for a period of ten days at a temperature of 21°±1° C., under conditions of controlled diet and water "ad libitum". Three days prior to the beginning of the test, the animals were divided in groups of ten for the purpose of achieving randomization. Each does has been tested on three groups of animals.

The sensitization has been achieved by administration of whole horse serum, that is horse serum not treated with preservatives, through the endovenous route in the amount of 1 ml/guinea pig, the horse serum having been diluted with physiological saline solution in the ratio of 1:10. After 14 days, there are administered the solutions of the substances in the test and physiological solution to the animals kept as control through the parenteral route. Simultaneously, through the intravenous route, 1 ml/guinea pig of undiluted horse serum has been administered as the agent which prompts the anaphylaxis. The percentage of mortality is determined after 12 hours. The results are reported herinbelow in Table 2.

TABLE 2

| COMPOUND | DOSE,mg/kg | % MORTALITY |
| --- | --- | --- |
| Physiological Solution | — | 80 |
| 6-α-M-P | 2.5 | 75 |
| 6-α-M-P | 5 | 71 |
| 6-α-M-P | 10 | 65 |
| 6-α-M-P | 15 | 57 |
| 6-α-M-P + L-A.M. | 2.5 + 1.3 | 53 |
| 6-α-M-P + L-A.M. | 5 + 2.6 | 38 |
| 6-α-M-P + L-A.M. | 10 + 3.9 | 21 |
| 6-α-M-P + L-A.M. | 15 + 10 | 12 |

The meaning of the symbols and abbreviations are explained under Table 1.

What is claimed is:

1. A pharmaceutical composition consisting essentially of a salt of 6-α-methyl-prednisolone-21-hemisuccinate and a L-arginine ester in the form of the hydrochloride salt.

2. A pharmaceutical composition according to claim 1 wherein said salt of 6-α-methyl-prednisolone-21-hemisuccinate and said L-arginine ester are in molar ratio of 1:1.

3. The method of protecting a living subject against shocks which consists of administering to said subject through the parenteral route an effective amount of a composition containing a salt of 6-α-methyl-prednisolone-21-hemisuccinate and the methyl ester of L-arginine in the form of the hydrochloride salt.

4. The method according to claim 3 wherein said composition contains said salt of 6-α-methyl-prednisolone-21-hemisuccinate and L-arginine methyl ester in the molar ratio of 1:1.

* * * * *